Dec. 20, 1932. J. DIDATO Plant Pat. 50
HYBRID TEA ROSE
Filed June 8, 1932
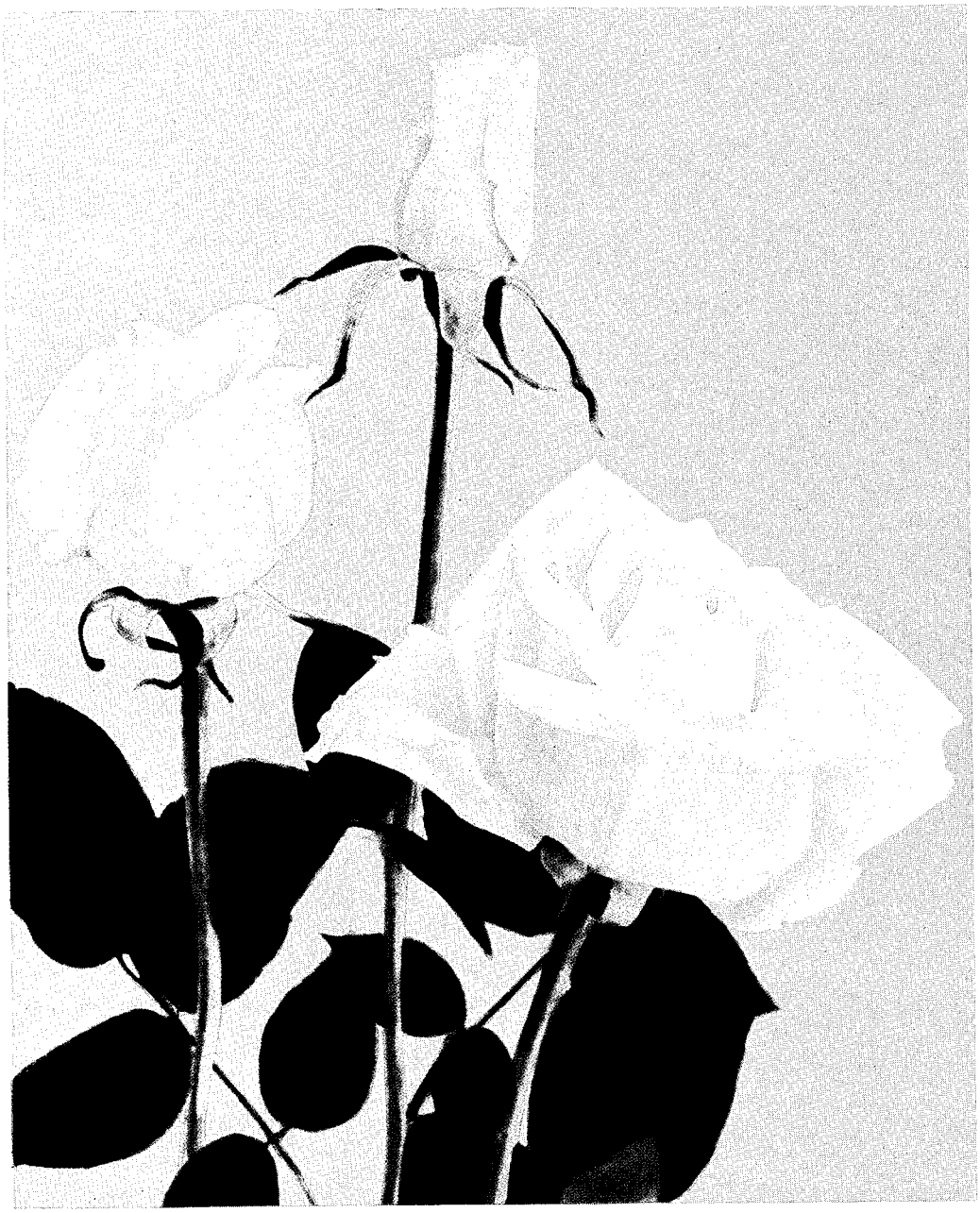
Inventor
James Didato
By Orville M. Kile
Plant Patent Agent Patented Dec. 20, 1932

Plant Pat. 50

UNITED STATES PATENT OFFICE

JAMES DIDATO, OF MIDDLESEX, NEW JERSEY

HYBRID TEA ROSE

Application filed June 8, 1932. Serial No. 616,154.

My new variety of rose was developed by me as a sport of the well known variety "President Hoover". I first discovered this bud sport on or about March 3, 1931. After observing and testing this plant for a period, I reproduced it asexually and thus determined that it would reproduce true to type.

My new variety has many of the desirable physical qualities of the "President Hoover" variety but differs from it radically in color of blossoms. In this latter respect it resembles the variety Joanna Hill except that the outer whorls of petals in my new variety are of a reddish-pink color. The color of the half opened flower of my variety is somewhat lighter yellow than that of Joanna Hill.

The accompanying illustration shows in full color a tightly rolled bud, a bud beginning to open, and a flower about two-thirds open, also stems and foliage.

The following is a detailed description of this variety of rose but it must be understood that there may be some variations as between particular specimens;

A bush or upright hybrid tea rose of medium height.

*Stems.*—Medium stout to stout, straight rather than zigzag, with medium number of prominent pinkish thorns pointing sharply downward, but none occurring on the first 6 or 7 inches of the stem immediately below the blossom. This portion of the stem is beset with a few small spines. The leaf branches on the flower-bearing stems are set 2¼ to 2½ inches apart.

Leaves are of medium size and pointed rather than ovate, the largest measuring about 2½ inches in length. Arranged 3 to a leaf-branch just below the blossom, increasing to 5 to a leaf branch until the fourth or fifth leaf branch is reached when the number of leaves may increase to 6 or 7. The petioles usually have a suggestion of brown on the upper surface. One to five distinct spines are ordinarily found on the under side of the central stem of the leaf branch. The leaves are of a light green color—approximately "forest green" (Plate XVII of Ridgeway's Color Guide and Nomenclature, Edition of 1912)—not glossy, and the serrations on the edges are very shallow. The leaves tend to the flat rather than the crinkled form.

Stipules are rather narrow, though long, and the small sharp tips are set approximately at right angles to the petioles.

*Hips.*—Medium width and moderately tapering.

Buds are pointed, about 1½ inches long in June, and begin to open with two outside petals forming winged effects suggestive of a sweet-pea.

*Sepals.*—Five in number, long, and one or more on each flower foliaceous in character.

Flowers are borne singly and at the season of examination (June) were 3½ to 4 inches across the top when fully opened. The central portion of the flower remains pointed or conical in shape until the blossom approaches the full-blown stage. The outer petals roll or curl back only moderately.

*Petallage.*—The flower in June has but 24 to 26 petals, but all except five or six of the central petals are very large and both the bud and the blossom create the impression of adequate substance. The flower is well supplied with yellow stamens mounted by brown-edged anthers, and with pink-topped, greenish hair-covered pistils, but the number of these sex-organs is medium rather than great.

*Color.*—The color of the bud before opening is predominantly a reddish-pink—"rose color" to "rose pink" (Plate XII Ridgeway's Color Guide and Nomenclature), but as it begins to open the color of the central portion of the flower is light yellow—"citron yellow" (Plate XVI of Ridgeway's Color Guide and Nomenclature). As the flower opens more fully the light yellow effect changes to a darker tone. The reddish shades of the outer petals also gradually change to light pink. These successive changes in predominating color effects have several causes: (1) The decidedly reddish color of the outer whorl of petals which gives the color of the bud. (2) As these outer petals turn back the under side of the inner whorls of petals are disclosed. These are colored light yellow. (3) As these inner whorls of petals open and turn back their inside surfaces become visible and the outside surfaces are largely concealed.

These inner surfaces show extremely slight suffusions of pink—not enough to be recognized as pink except on close examination, but enough to create a darker tone. (4) During this succession of color changes the outer whorl of petals has not only curled back into partial concealment, but the color has faded to a much lighter tint.

It will be seen, therefore, that when displayed in a vase a bouquet of this variety made up of flowers in different stages of maturity, would create a great variety of color effects.

One, or sometimes more than one, of the inner petals bears a narrow light pink streak down its central area. Even the outer petals that are a decided pink on their upper surface have yellow bases on both upper and lower surfaces —"strontian yellow" (Plate XVI of Ridgeway's Color Guide and Nomenclature)—and the lower surface is usually half to two-thirds yellow or only touched with pink at the edges.

My new variety is easily distinguished from all other varieties by the unusual combination of colors, beginning with the tightly rolled bud, and progressing through the several successive color changes above described.

What I claim as new is:

The variety of hybrid tea rose herein shown and described, characterized particularly by its reddish-pink buds, opening into a yellow flower with pink-tipped outer petals.

In testimony whereof I affix my signature.

JAMES DIDATO.